US010345321B2

United States Patent
Gerlinger et al.

(10) Patent No.: US 10,345,321 B2
(45) Date of Patent: Jul. 9, 2019

(54) AUTOMATIC ANALYZER AND METHOD

(71) Applicant: Endress+Hauser Conducta GmbH+Co. KG, Gerlingen (DE)

(72) Inventors: Anja Gerlinger, Stuttgart (DE); Matthias Knopp, Weissach-Flacht (DE); Tilman Benkert, Stuttgart (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 163 days.

(21) Appl. No.: 15/347,894

(22) Filed: Nov. 10, 2016

(65) Prior Publication Data

US 2017/0138973 A1     May 18, 2017

(30) Foreign Application Priority Data

Nov. 13, 2015   (DE) .......................... 10 2015 119 608

(51) Int. Cl.
| | | |
|---|---|---|
| *G01N 35/10* | (2006.01) | |
| *G01N 21/03* | (2006.01) | |
| *G01N 35/00* | (2006.01) | |
| *G01N 33/18* | (2006.01) | |

(52) U.S. Cl.
CPC ............ *G01N 35/10* (2013.01); *G01N 21/03* (2013.01); *G01N 33/18* (2013.01); *G01N 35/00712* (2013.01); *G01N 35/00732* (2013.01); *G01N 35/00871* (2013.01); *G01N 2201/061* (2013.01)

(58) Field of Classification Search
None
See application file for complete search history.

(56) References Cited

U.S. PATENT DOCUMENTS 5,590,052 A  *  12/1996  Kopf-Sill et al. ............ 634/498

FOREIGN PATENT DOCUMENTS

| CN | 104345033 A | 2/2015 |
|---|---|---|
| DE | 1022822 | 1/1958 |
| DE | 284976 A5 | 11/1990 |
| DE | 102009029305 A1 | 3/2011 |
| DE | 102011075762 A1 | 11/2012 |
| DE | 102011088235 A1 | 6/2013 |

(Continued)

OTHER PUBLICATIONS

Machine-generated translation of reference N (Bei et al., pp. 1-5), 2015.*

*Primary Examiner* — Kathryn Wright
(74) *Attorney, Agent, or Firm* — Kelly J. Smith; PatServe

(57) ABSTRACT

The present disclosure includes an automatic analyzer and a method for the determination of a measurand dependent upon the concentration of one or more ingredients of a measuring fluid. The analyzer includes a measuring cell includes a cuvette and a sensing element, the sensing element including at least one radiation source and at least one detector configured to generate measurement signals, a control and evaluation unit that is connected to the sensing element to receive and process measurement signals of the sensing element, and a delivery and metering unit that can be controlled by the control and evaluation unit, where the control and evaluation unit is configured to control the delivery and metering unit to transport measuring fluid into the cuvette and to monitor the transport of the measuring fluid into the cuvette by means of the sensing element.

8 Claims, 1 Drawing Sheet

(56) References Cited

FOREIGN PATENT DOCUMENTS

| | | | | |
|---|---|---|---|---|
| JP | 2000275252 | A | 10/2000 | |
| JP | 2003057248 | A | 2/2003 | |
| JP | 2003194709 | A | 7/2003 | |
| JP | 2015-025792 | A * | 2/2015 | ............. G01N 21/17 |

* cited by examiner

AUTOMATIC ANALYZER AND METHOD

CROSS-REFERENCE TO RELATED APPLICATION

The present application is related to and claims the priority benefit of German Patent Application No. 10 2015 119 608.5, filed on Nov. 13, 2015, the entire contents of which are incorporated herein by reference.

TECHNICAL FIELD

The present disclosure relates to analyzers for the determination of a measurand dependent upon the concentration of one or more ingredients of a measuring fluid.

BACKGROUND

In order to determine the composition of measuring fluids, such as pure liquids, liquid mixtures, emulsions, or suspensions, analyzers are often used in process measurement technology or in environmental analytics. An analyzer generally comprises a sensing element which is designed to generate a measurement signal dependent upon at least one analytical measurand, as well as an electronic evaluation unit which from the measurement signal determines a measured value representing the current value of the at least one analytical measurand in the measuring fluid. The electronic measuring unit can be integrated at least partially into a control and evaluation unit of the analyzer, said control and evaluation unit comprising display and input means, by means of which a user can enter and retrieve information.

The analytical measurand can, for example, be a measurand dependent upon the concentration of one or more ingredients of the measuring fluid. Such measurands are, for example, the concentration or activity of certain ion types, such as nitrate, phosphate, or ammonium in water samples, or even sum parameters of water analytics, such as COD (chemical oxygen demand), TOC (total organic carbon), TNb (total nitrogen), or TP (total phosphorus), which depend upon the concentration of several different ingredients in the sample. The measuring fluid can be taken automatically by means of an automatic sample preparation unit at a sampling point from a process or from a body of water to be examined and held available in a so-called sample receiving vessel. In order to determine a measured value of the measurand, an analyzer is often designed to take a sample of the liquid contained in the sample receiving vessel and to preprocess it for example, by adding reagents. The ingredient(s) to be determined can even be present in the measuring fluid in an undissolved state, which frequently requires dissolution to be carried out before measurement of the measurand by means of the sensing element.

By means of the sensing element, the analyzer determines one or more measured values of a parameter of the possibly preprocessed sample, said parameter correlating with the measurand to be determined and dependent upon the concentration or activity of one or more ingredients of the measuring fluid. The preprocessing of the sample often comprises the addition of one or more reagents to the sample. The reagents are generally selected such that the preprocessing results in a chemical reaction involving the ingredient(s), upon the concentration or activity of which the measurand to be determined depends. The reaction product can be detected by means of the sensing element. The parameter detected by the sensing element can correlate especially with the concentration of the reaction product, especially with an intensity of a coloration of the preprocessing liquid sample, said coloration being caused by the reaction product. Oftentimes, the sensing element is designed as a photometric or spectrometric sensing element that detects an absorption or extinction of the preprocessed sample at one or more wavelengths as a parameter correlating with the measurand and generates one or more electrical measurement signals representing this absorption or extinction. Based upon the measurement signals of the sensing element, the control and evaluation unit of the analyzer can derive measured values of the measurand for example, by using a stored correlation rule, possibly determined by a calibration, in the form of a table or a function.

Such analyzers are known, for example, from DE 10 22 822 A1, DE 10 2009 029 305 A1, or DE 10 2011 075 762 A1.

In DE 10 2011 088 235 A1, for example, an analyzer for the automatic determination of a measurand dependent upon a concentration of an ingredient of a measuring fluid is described, which comprises a sample receiving vessel as well as one or more liquid tanks for one or more reagents, a cuvette for receiving a reaction mixture generated by mixing a liquid sample taken from the sample receiving vessel with one or more reagents, and a sensing element for providing one or more measurement signals correlating with the measurand. The analyzer comprises a control and evaluation unit that is designed to control the analyzer and to determine the measurand based upon the measurement signals provided by the sensing element. The analyzer also comprises a delivery and metering unit controlled by the control and evaluation unit, to deliver and meter the liquid sample and liquids from the liquid tanks into the cuvette.

The fill level of the sample receiving vessel can be monitored in such analyzers by means of a suitable level sensor, in order to ensure that only in the presence of a sufficient quantity of measuring fluid is a new measurement cycle of the analyzer started. If this monitoring, however, fails, or if the liquid lines that connect the sample receiving vessel to the sensing element are clogged or have leaks, it can happen that the sample taken from the sample receiving vessel for preprocessing has a volume that is less than the sample volume specified by the control and evaluation unit or that no measuring fluid at all arrives in the cuvette. Since the liquid lines in conventional analyzers have relatively small cross-sections in order to manage with the smallest sample and reagent volumes possible, gas bubbles occurring in the liquid lines can also result in the sample volumes being too small. However, if the sample volume actually delivered does not match the sample volume specified by the control and evaluation unit, or if no measuring fluid arrives in the cuvette, incorrect measurements can result.

Even if non-plausible measured values due to incorrect measurements are detected, an evaluation of the source of the error based only upon the current measured values is problematic.

Accordingly, there remains a need for further contributions in this area of technology to enable a means of ensuring a desired sample volume.

SUMMARY

It is therefore the aim of the present disclosure to provide a generic analyzer that overcomes the disadvantages of the prior art. The analyzer of the present disclosure prevents undetected incorrect measurements due to a sample volume that is too small having been transported into the cuvette. This aim is achieved according to the present disclosure by an analyzer according to claim 1 and a method according to claim 12. Advantageous embodiments are specified in the dependent claims.

The automatic analyzer according to the present disclosure for the determination of a measurand dependent upon the concentration of one or more ingredients of a measuring fluid includes a measuring cell having a cuvette and a sensing element, where the sensing element includes at least one radiation source that is designed to emit measuring radiation, and at least one detector that is designed to generate measurement signals that are dependent upon an intensity of the measuring radiation emitted by the radiation source, the intensity impinging upon the detector, and where the radiation source and the detector are oriented toward each other and toward the cuvette such that the measuring radiation passes through the cuvette before it strikes the detector. The analyzer further includes a control and evaluation unit that is connected to the sensing element to receive measurement signals of the sensing element and that is designed to process the received measurement signals, a sample receiving vessel used to receive the measuring fluid, the sample receiving vessel being connected to the cuvette via a liquid line system, and a delivery and metering unit that can be controlled by the control and evaluation unit, where the control and evaluation unit is designed to control the delivery and metering unit to transport measuring fluid from the sample receiving vessel into the cuvette and to monitor the transport of the measuring fluid into the cuvette by means of the sensing element.

The monitoring of the transport of the measuring fluid into the cuvette may include a check as to whether the delivery and metering unit transports or has transported any measuring fluid into the cuvette at all. If the liquid line system that connects the sample receiving vessel to the cuvette is clogged or has a significant leak, or if no measuring fluid is present in the sample receiving vessel, this results in the delivery and metering unit controlled by the control and evaluation unit to transport a specified volume of the measuring fluid not actually transporting any measuring fluid into the cuvette. By means of the sensing element, the control and evaluation unit can check whether measuring fluid has actually arrived in the cuvette. If no measuring fluid is present in the cuvette, the control and evaluation unit can emit an appropriate warning signal or initiate further steps, e.g., a new attempt to transport measuring fluid from the sample receiving vessel into the cuvette by means of the delivery and metering unit, or, in case of a persistent error, to interrupt the measuring operation of the analyzer.

The monitoring of the transport of the measuring fluid into the cuvette can also include the control and evaluation unit checking whether a discrepancy exists between a measuring fluid volume actually transported into the cuvette and a volume specified by the control and evaluation unit to control the delivery and metering unit. If, due to gas bubbles, a smaller volume of measuring fluid arrives in the cuvette than the volume specified by the control and evaluation unit, the control and evaluation unit can determine this by means of the sensing element and output an appropriate warning message.

The control and evaluation unit can include a data processing unit, e.g., an electronic data processing unit, that has at least one processor, especially a microprocessor, the data processing unit including a memory, in which one or more operating programs are provided that are used to control the analyzer and to evaluate the measurement signals sent by the sensing element. The data processing unit, especially the electronic data processing unit or the processor, can be designed in this case to execute the operating program stored in the memory or several operating programs stored in the memory, to control the analyzer and/or to evaluate the measurement signals sent by the sensing element to the data processing unit. The control and evaluation unit can also include an input interface, such as a human-machine interface (HMI) for an operator to enter commands or parameters, and/or an interface for receiving commands, parameters, or other data from a superordinate unit, such as a process control system, a measuring transducer, a programmable logic controller, an operator unit, especially a portable operator unit, such as a mobile telephone or a tablet PC or notebook. In addition, the control and evaluation unit can also include an output device to output data, especially measurement results or operating information, to a user, e.g., via an HMI, or an interface to output data to the superordinate unit.

The liquid line system that connects the sample receiving vessel to the cuvette can, for example, include at least one liquid line, the first end of which is connected to the sample receiving vessel for example, by the liquid line opening into the sample receiving vessel or by the first end being connected to another liquid line that opens into the sample receiving vessel. In this embodiment, the second end of the at least one liquid line is connected to the cuvette for example, by the liquid line opening with this second end into the cuvette or by the second end being connected to another liquid line that opens into the cuvette. In the liquid path running through the liquid line system or the at least one liquid line, one or more valves can be arranged. Furthermore, the liquid line system can also include additional liquid lines that connect additional liquid tanks of the analyzer to the cuvette.

The delivery and metering unit can comprise one or more pumps that are used to transport liquids through liquid lines of the analyzer. The control and evaluation unit can be connected to drives of the pumps to operate and control these pumps and can further be designed to control the pumps in accordance with an operating program stored in a memory of the control and evaluation unit, e.g., one of the operating programs mentioned above.

In order to transport measuring fluid from the sample receiving vessel into the cuvette, the control and evaluation unit can be connected to at least one pump that is arranged in the liquid path running through the liquid line system between the sample receiving vessel and the cuvette, especially in the at least one liquid line mentioned above. The control and evaluation unit can include an operating program and be designed to control the transport of the measuring fluid through the liquid path by executing the operating program.

In at least one embodiment of the analyzer, in order to monitor the transport of the measuring fluid into the cuvette, the control and evaluation unit can be designed to detect a first measurement signal of the sensing element when the cuvette is empty, to control the delivery and metering unit to transport a specified volume of the measuring fluid from the sample receiving vessel into the cuvette, and, at the same time or subsequently, detect at least one second measurement signal of the sensing element, and to determine, based upon the detected measurement signals, whether a volume of the measuring fluid transported into the cuvette matches the specified volume.

In order to monitor the transport of the measuring fluid into the cuvette, the control and evaluation unit can further also be designed to determine a test value from the first measurement signal and the second measurement signal and to compare it to at least one reference value that can be stored in a memory of the control and evaluation unit. In this case, the test value is a measurement for the difference of the absorption or extinction of the measuring radiation, radiated through the cuvette, of the sensing element in the empty measurement and in the measurement after a liquid transport into the cuvette has been carried out. The reference value can be specified such that it corresponds to an extinction difference or an absorption difference when the cuvette is empty and when the cuvette is filled with the specified volume of the measuring fluid.

The control and evaluation unit can, for example, be designed to determine a first value from the first measurement signal, to determine a second value from the second measurement signal, and to determine a test value from the first and the second values, for example, by division or subtraction, and to compare this test value to the reference value.

In order to monitor the transport of the measuring fluid into the cuvette, the control and evaluation unit can further be designed to determine a deviation of the test value from the reference value, for example, by division or subtraction. The determined deviation is an indicator as to whether a sufficient volume of the measuring fluid was transported into the cuvette.

In one embodiment, the sensing element can include several radiation sources, wherein each of the radiation sources is designed to emit measuring radiation of a certain wavelength range. Advantageously, the wavelength range of the measuring radiation emitted by each of the radiation sources differs from the wavelength ranges of the measuring radiation emitted by all the other radiation sources, so that all radiation sources emit measuring radiation of different wavelength ranges.

In this embodiment, the control and evaluation unit can be designed to excite several or all radiation sources of the sensing element, one after the other, to emit measuring radiation, and, by means of the detector, to detect measurement signals dependent upon an intensity of the measuring radiation of each of the excited radiation sources after passing through the cuvette.

In this embodiment, in order to monitor the transport of the measuring fluid into the cuvette, the control and evaluation unit can be designed to detect first measurement signals of the detector dependent upon the intensity of the measuring radiation of the excited radiation sources after passing through the cuvette when the cuvette is empty and to detect, during or after the transport of the sample from the sample receiving vessel into the cuvette, second measurement signals of the detector dependent upon the intensity of the measuring radiation of the radiation sources controlled to emit measuring radiation.

The control and evaluation unit can further be designed to determine a first value from the first measurement signals, especially by summation or weighted summation, and to determine a second value from the second measurement signals, especially by summation or weighted summation, and to determine a test value from the first and the second values, especially by subtraction or division. The advantage of determining a test value based upon several measurement signals consists in the differences in the absorption or extinction of the measuring radiation of the individual radiation sources when cuvette is filled and empty being added up, which facilitates a distinction between an empty and a filled cuvette based upon the measurement signals of the sensing element.

The control and evaluation unit can further be designed to compare the test value to at least one reference value stored in a memory and to monitor the transport of the measuring fluid into the cuvette based upon this comparison. The reference value can be specified such that it corresponds to a cumulative extinction or absorption difference, generated from the first and second measurement signals, of the measuring radiation of the radiation sources used to monitor the transport of measuring fluid into the cuvette when the cuvette is empty and when the cuvette is filled with a specified volume of the measuring fluid. A deviation between a test value, determined on the basis of the first measurement signals and the second measurement signals detected using the same radiation sources of the sensing element, and the reference value is an indicator that no measuring fluid, or a volume of measuring fluid that is too small, was transported into the cuvette.

The analyzer can further include at least one liquid tank, which contains another liquid, where the liquid tank is connected to the cuvette via the liquid line system and where the control and evaluation unit is designed to detect at least one third measurement signal of the sensing element when the cuvette is empty, to control the delivery and metering unit to transport the other liquid from the liquid tank into the cuvette, and, during or after controlling the delivery and metering unit, to transport the other liquid into the cuvette, to detect at least one fourth measurement signal of the sensing element, and to monitor the transport of the other liquid into the cuvette based upon the third and fourth measurement signals. The monitoring can advantageously be carried out in a completely analog manner, as described above for the monitoring of the transport of the measuring fluid into the cuvette.

The other liquid can be a reagent to be added to the measuring fluid to determine the measurand, a standard solution, or a cleaning liquid.

In order to perform a measurement of the measurand, the control and evaluation unit can be designed to transport a specified volume of the measuring fluid as sample in the cuvette by means of the delivery and metering unit and, prior to the introduction into the cuvette or in the cuvette with the other liquids used as reagents, to mix the sample for preprocessing. In order to determine a measured value of the measurand, the control and evaluation unit can further be designed to detect at least one measurement signal by means of the sensing element while the preprocessed sample is contained in the cuvette, and to determine a measured value of the measurand based upon the at least one measurement signal. The control and evaluation unit can further be designed to drain liquid, especially the preprocessed sample, from the cuvette by means of the delivery and metering unit.

These steps form a measurement cycle. The control and evaluation unit is designed to rinse the cuvette between measurement cycles at least once with the measuring fluid. Advantageously, the transport of the measuring fluid into the cuvette is monitored in the meantime according to the method described below.

The present disclosure also includes a method for monitoring a transport of measuring fluid into a cuvette of an automatic analyzer, according to at least one of the embodiments described above. The method includes controlling a delivery and metering unit by means of a control and evaluation unit to transport measuring fluid from a sample receiving vessel via a liquid line system into the cuvette and monitoring of the transport of the measuring fluid into the cuvette by the control and evaluation unit by means of a sensing element that comprises at least one radiation source and at least one detector, which are oriented toward each other and toward the cuvette such that measuring radiation emitted by the radiation source passes through the cuvette before it strikes the detector.

The monitoring of the transport of the measuring fluid into the cuvette by the control and evaluation unit can include exciting the at least one radiation source to radiate measuring radiation into the cuvette and detecting at least one first measurement signal of the detector dependent upon an intensity of the measuring radiation after passing through the cuvette when the cuvette is empty, during or after controlling the delivery and metering unit to transport a specified volume of measuring fluid into the cuvette, exciting the radiation source to radiate measuring radiation into the cuvette and detecting at least one second measurement signal of the detector dependent upon the intensity of the measuring radiation after passing through the cuvette, and determining, based upon the detected measurement signals, whether a volume of the measuring fluid transported into the cuvette matches the specified volume.

These steps can be performed automatically by the control and evaluation unit.

The method can further include determining a test value from the first and the second measurement signals and comparing the test value to at least one reference value, for example, one stored in a memory of the control and evaluation unit.

As described above, the test value is a measurement for the difference of the absorption or extinction of the measuring radiation, radiated through the cuvette, of the sensing element in the empty measurement and in the measurement after a liquid transport into the cuvette has been carried out. The reference value can be specified such that it corresponds to an extinction difference or an absorption difference of the measuring radiation when the cuvette is empty and when the cuvette is filled with the specified volume of the measuring fluid.

The determination of the test value can include determining a first value from the first measurement signal, determining a second value from the second measurement signal, and determining a test value from the first and the second values, especially by division or subtraction.

In one embodiment, the method can be performed using several radiation sources that emit, in particular, measuring radiation of different wavelength ranges. In such an embodiment, the method further includes exciting several radiation sources of the sensing element one after the other to emit measuring radiation of a respectively certain wavelength range into the empty cuvette and detecting first measurement signals of the detector, where each of the first measurement signals depends upon the intensity of the measuring radiation emitted by one of the radiation sources, after passing through the empty cuvette, and exciting the several radiation sources one after the other to emit measuring radiation of a respectively certain wavelength range into the cuvette during or after controlling the delivery and metering unit to transport the specified volume of the measuring fluid from the sample receiving vessel into the cuvette and detecting second measurement signals of the detector, where each of the second measurement signals depends upon the intensity of the measuring radiation emitted by one of the radiation sources, after passing through the cuvette during or after controlling the delivery and metering unit to transport the measuring fluid into the cuvette.

A first value can be determined from the first measurement signals, for example, by summation or weighted summation, and a second value can be determined from the second measurement signals, for example, by summation or weighted summation, wherein a test value is determined from the first and the second values, for example, by subtraction or division.

The test value can be compared to a reference value stored in a memory. Based upon the comparison, the control and evaluation unit can monitor the transport of the measuring fluid into the cuvette. It can, for example, determine whether any fluid arrived in the cuvette at all or whether a sufficient volume, i.e., a volume substantially corresponding to a specified volume, of the measuring fluid was transported into the cuvette.

In another embodiment, in order to monitor the transport of the measuring fluid into the cuvette, it can be detected, based upon the at least one second measurement signal, when a liquid-air boundary moving through the cuvette during the transport of the sample into the cuvette passes a beam path extending substantially orthogonally to a direction of movement of the liquid-air boundary between the at least one radiation source and the detector.

A method for monitoring the transport of additional liquids held available in the liquid tanks of the analyzer, such as cleaning liquids, standard solutions, or reagents, into the cuvette can be designed in the same way as described above for the monitoring of the transport of measuring fluid into the cuvette.

BRIEF DESCRIPTION OF THE DRAWINGS

The present disclosure is explained in further detail below on the basis of the embodiment shown in the figure. Illustrated are.

DETAILED DESCRIPTION

Figure 1:
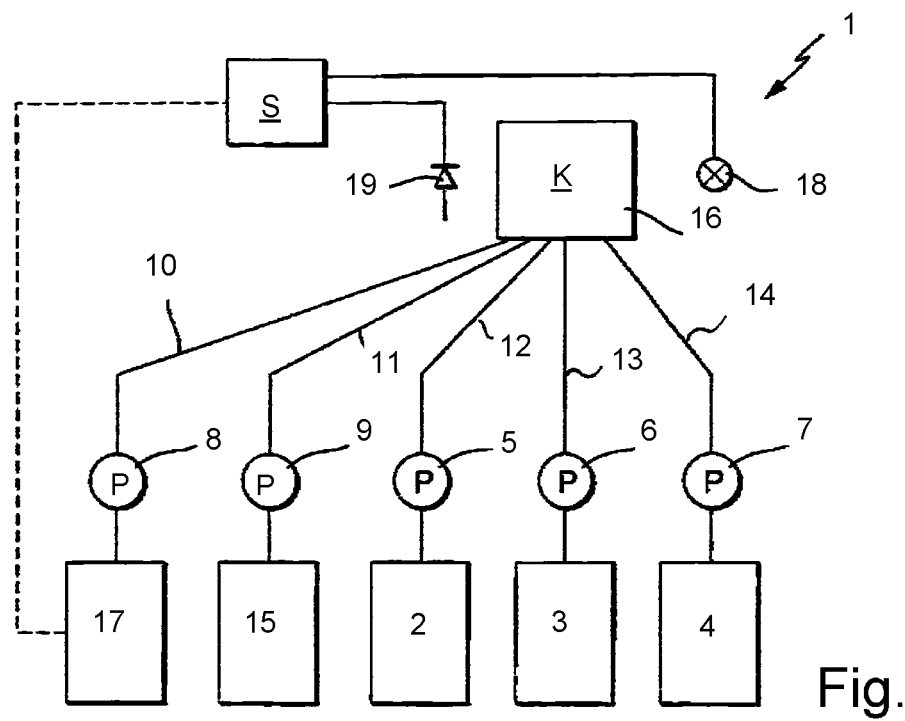
FIG. 1 shows a schematic representation of an automatic analyzer for the determination of a measurand dependent upon a concentration of one or more ingredients of a measuring fluid.

FIG. 1 schematically shows an analyzer 1 for the determination of a measurand dependent upon the concentration of one or more ingredients of a liquid sample. In the present example, the analyzer 1 is designed as a water analyzer for the determination of an ion concentration, e.g., of ammonium or phosphate, in a water sample. The analyzer 1 includes a measuring cell 16, several liquid tanks 2, 3, 4, and 15, a system of liquid lines 10, 11, 12, 13, 14, and a delivery and metering unit that includes a variety of pumps 5, 6, 7, 8, 9 and possibly valves (not shown) for controlling the liquid transport. The pumps 5, 6, 7, 8, 9 may, for example, be membrane pumps, piston pumps, syringe pumps or peristaltic pumps. The pumps 5, 6, 7 may be used to transport and meter liquids contained in the liquid tanks 2, 3, 4, respectively, via the liquid lines 12, 13, 14 to a cuvette K of the measuring cell 16. In addition, the analyzer 1 includes a waste tank 15 that is connected to the cuvette K via a liquid line 11. By means of the pump 9, liquid can be transported from the cuvette K into the waste tank 15. The analyzer further includes a sample receiving vessel 17, in which is contained a measuring liquid that was taken from a sampling point of, for example, a process or a body of water and possibly filtered. In order to perform a measurement, the analyzer 1 takes from the sample receiving vessel 17 a specified volume of the measuring fluid that is used as sample for the measurement. The sample receiving vessel 17 is connected to the cuvette K via the supply line 10. The pump 8 is used to transport and meter the sample into the cuvette K.

In addition to the cuvette K, the measuring cell 16 includes a sensing element that is used to detect measured values of the measurand to be determined by the analyzer 1. The sensing element includes at least one radiation source 18 emitting a measuring radiation, e.g., a light-emitting diode, and at least one detector 19, which are arranged relative to the cuvette K, which is transparent to the measuring radiation, such that the measuring radiation passes through a liquid contained in the measuring cell 16, such as a sample preprocessed with reagents, and the measuring radiation transmitted through the liquid strikes the detector 19. The detector 19 is designed to convert the received radiation intensity into an electrical measurement signal of the sensing element.

The cuvette K consists of a material that is transparent to the measuring radiation. If the measuring radiation is within the ultraviolet to visible (UV/Vis) range of the electromagnetic spectrum, glass or quartz glass is a suitable material.

The sensing element can also include a plurality of radiation sources in the form of individual light-emitting diodes that are designed to emit measuring radiation of different wavelength ranges. The sensing element can include as the detector 19 a photo diode, a photo diode array, or a CCD array.

The analyzer 1 can be operated fully automatically. For this purpose, it has a control and evaluation unit S that, in the example shown here, also provides the functions of an evaluation unit such as the determination of a measurand based upon a measured value detected by the sensing element. The control and evaluation unit S includes a data processing unit having a memory, in which are provided one or more operating programs that are used to control the analyzer 1 and evaluate the measurement signals delivered by the sensing element. The data processing unit can also include an input device for an operator to input commands or parameters and/or an interface to receive commands, parameters, or other data from a superordinate unit, such as a process control system. In addition, the control and evaluation unit S may also include an output device to output data such as measuring results or operating information to a user or an interface to output data to the superordinate unit. The control and evaluation unit S is connected to drives of the pumps 5, 6, 7, 8, 9, and to valves (not shown) in order to automatically operate them to transport liquids from the sample receiving vessel and the storage tanks 2, 3, 4, 15 into the cuvette K. The control and evaluation unit S is also connected to the sensing element in order to control it and to determine from the measurement signals of the detector 18 the measurand to be determined.

The storage tank 4 may contain a reagent that is mixed with the sample removed from the sample receiving vessel 17 to process it. The reagent can, for example, be selected such that it reacts with the ingredient(s), upon the concentration of which the measurand depends, while forming a colored reaction product. The intensity of the coloration is then a measurement for the concentration to be determined or for the measurand to be determined. The wavelength of the measuring radiation emitted by the radiation source 18 is in this case adapted to the coloration of the reaction product and is evaluated accordingly by the detector 19 or by the control and evaluation unit S. Instead of a single reagent as in the example shown here, several reagents may also be used, depending upon the measurand to be determined. In this case, the analyzer 1 includes an appropriate number of storage tanks for the reagents needed.

In order to perform a measurement, the control and evaluation unit S performs a measurement cycle of the analyzer. At the beginning of the measurement cycle, the control and evaluation unit S first, by means of the pump 8, meters a specified quantity of the measuring fluid contained in the sample receiving vessel 17 in the present example, a water sample as sample into the cuvette K. At the same time or subsequently, the control and evaluation unit S controls the pump 7 to transport a specified quantity of the reagent contained in the liquid tank 4 into the cuvette K. Thus, the cuvette K in the example described here is also used as a mixing cell, in which the sample and the reagent are mixed. However, other embodiments are also possible, in which the reagent or several reagents are mixed with one another to process the sample before the sample preprocessed using the reagents is metered into the cuvette K.

In order to detect the measurand to be determined of the preprocessed sample contained in the cuvette K, the control and evaluation unit S operates the sensing element, wherein the control and evaluation unit S excites the radiation source 18 to emit measuring radiation, among other things. The detector 19 receives the measuring radiation after passing through the cuvette K and through the preprocessed sample contained therein and converts the measuring radiation intensity received into an analog or digital electrical measurement signal. The measurement signal is processed further by the control and evaluation unit S, which correlates the absorption or extinction of the measuring radiation by the sample, wherein the absorption or extinction is a parameter correlating with the measurand dependent upon the concentration of the ingredient(s).

The control and evaluation unit S analyzes the measurement signal, emitted by the sensing element, of the detector 19. The control and evaluation unit S can, for example, determine a value of the measurand in the physical units of the measurand from the measurement signal or a value derived therefrom based upon stored tables or based upon a stored calibration function and output it via a display device, such as a display, or via an interface to a superordinate unit.

After the measurand has been determined, the cuvette K is emptied by transporting the used liquid sample contained in the measuring cell into the waste tank 15 using the pump 9. The measurement cycle is thus completed.

The analyzer 1 has other storage tanks 2, 3 that may contain standard solutions for calibrations and/or cleaning solutions. By means of pumps 5, 6 associated with the storage tanks 2, 3, respectively, these solutions can be transported into the cuvette K via the lines 12, 13 in a manner controlled by the control and evaluation unit S and can be discharged via the line 11 into the waste tank 15 by means of the pump 9.

After one or more measurements have been performed, the control and evaluation unit S can perform a calibration of the analyzer 1 by transporting a calibration standard from the storage tank 2 into the cuvette K. The calibration standard is treated like a "real" sample from the sample receiving vessel 17 with the reagent that is being transported from the storage tank 4 into the cuvette K by means of the pump 7. By means of the sensing element, a measured value of the measurand is determined photometrically as described above, and an adjustment of the analyzer 1 is possibly performed, based upon the measured value known for the calibration standard.

The control and evaluation unit S is also designed to monitor the transport of measuring fluid from the sample receiving vessel 17 into the cuvette K, in order to detect incorrect measurements due to a missing sample or due to a sample volume that is too small having been metered into the cuvette K. For this purpose, the control and evaluation unit S includes an operating program that is used to perform the method described below for monitoring the transport of measuring fluids into the cuvette K.

After performing a measurement cycle according to the method described above, the cuvette K is initially empty, i.e., filled with air but no liquids, after the processed sample is discharged from the cuvette K into the waste tank 15. Prior to starting the next measurement cycle, a rinsing step is performed at least once or multiple times in which the cuvette K is rinsed with the measuring fluid. For this purpose, the control and evaluation unit S controls the pump 8 such that a specified volume of the measuring fluid is transported from the sample receiving vessel 17 via the line 10 into the cuvette K. Subsequently, the control and evaluation unit S controls the pump 9, to again drain the measuring fluid from the cuvette K via the line 11 into the waste tank 15. After draining the measuring fluid, the cuvette K is again empty or filled with air.

In order to monitor whether the measuring fluid is transported correctly and in sufficient quantity into the cuvette K in this rinsing step, the control and evaluation unit S detects at least one first measured value by means of the sensing element with the cuvette K being empty. During or after the transport of the measuring fluid within the scope of the rinsing step described, the control and evaluation unit S detects at least one second measured value by means of the sensing element.

The empty or air-filled cuvette K shows a different absorption or extinction behavior than the cuvette K filled completely or partially with the measuring fluid. A difference is therefore expected between the first measured value representing the extinction or absorption of the measuring radiation in the empty cuvette K and the second measured value representing the extinction or absorption of the measuring radiation in the cuvette K filled with measuring fluid. From the first and the second measured values, the control and evaluation unit S determines a test value, which represents a deviation of the second measured value from the first measured value. The test value can be determined, for example, by division or subtraction of the measured values.

By comparing the test value to at least one reference value, the control and evaluation unit can determine whether measuring fluid was present in the cuvette K during the detection of the second measured value or whether a sufficient volume of measuring fluid was transported into the cuvette K. If this is the case, an error of the analyzer can be deduced.

In the case where the test value is generated by subtracting the first measured value from the second measured value, the reference value can be zero, and thus represent the expected deviation of the first measured value from the second measured value for the case in which no measuring fluid actually arrives in the cuvette K during the controlling of the pump 8 to transport liquid into the cuvette. In the case where the test value is generated by division, the reference value can, accordingly, be 1.

If the test value corresponds to the reference value in these cases, or if the test value is within the specified tolerance value range surrounding the reference value, it can be concluded that no transport of the measuring fluid into the cuvette actually occurred by controlling the pump 8 to transport measuring fluid into the cuvette K. In this case, the control and evaluation unit S can output an error or warning message and/or not perform any additional measurement of the measurand. In this way, error messages due to a missing sample are avoided, or at least detected. On the other hand, if the test value differs from the reference value or is outside the tolerance value range, the control and evaluation unit S continues with a measurement cycle according to the method described above.

In addition or alternatively, the control and evaluation unit S can also compare the test value to at least one reference value representing an expected deviation of the absorption or extinction of the measuring radiation in the empty cuvette K from the absorption or extinction of the measuring radiation in the cuvette filled with measuring fluid. This reference value can, for example, have been determined by means of a one-time or regularly repeated calibration with the measuring fluid and stored in the memory of the control and evaluation unit S.

The control and evaluation unit S compares the determined test value to the at least one stored reference value by subtraction or division, for example. It is also possible to specify a tolerance value range, which surrounds the reference value as an interval, for the comparison of the test value to the reference value. To the extent that the test value is within the tolerance value range, the transport of the measuring fluid into the cuvette K may not be determined to be erroneous by the control and evaluation unit S. In the next step, the control and evaluation unit S in this case performs another measurement according to the method described above.

On the other hand, if the test value deviates from the reference value, or if the test value is outside the tolerance value range, it can be concluded that no transport or no sufficient transport of the measuring fluid into the cuvette actually occurred by controlling the pump 8 to transport measuring fluid into the cuvette K. In this case, in order to avoid undetected error conditions, the control and evaluation unit S can output an error or warning message and/or not perform any additional measurement cycles.

The same method according to one of the embodiments described above can be used to monitor the transport of other liquids contained in the liquid tanks 2, 3, 4 into the cuvette K. In this way, it can be ensured that a sufficient quantity of reagents, cleaning liquid, or standard liquid is present, to ensure a reliable operation of the analyzer.

An alternative or additional embodiment of monitoring the transport of the measuring fluid or other liquids into the cuvette K can occur during the transport of the liquid into the cuvette. At the moment when the liquid-air boundary passes the beam path between the radiation source 18 and the detector 19, a momentarily significant signal change of the detector 19 occurs. The control and evaluation unit S can be designed to output an error message when this signal change is missing, in order to ensure that a sufficient volume of measuring fluid was transported into the cuvette K.

Figure 2:
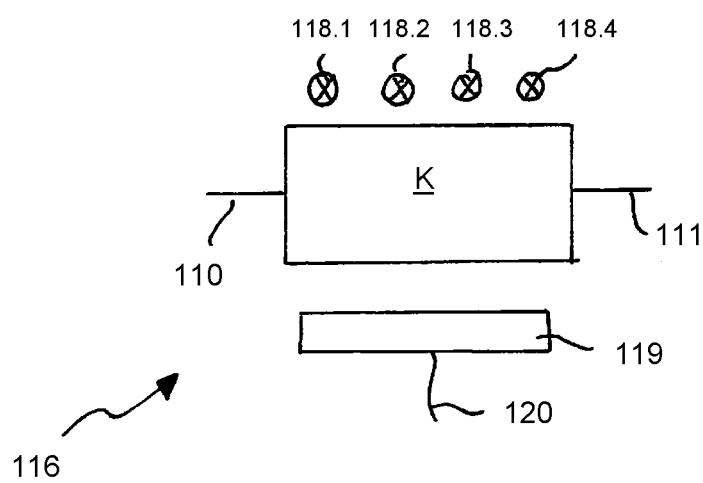
FIG. 2 shows a schematic representation of a measuring cell of an analyzer like the one illustrated in FIG. 1.

FIG. 2 schematically shows an alternative embodiment of the measuring cell 116 of an automatic analyzer, such as the one described based upon FIG. 1. The automatic analyzer, in which the measuring cell is contained, includes, in particular, a control and evaluation unit for the completely automatic control of the analyzer.

The measuring cell 116 includes a cuvette K having an inlet 110, via which it is connected to a sample receiving vessel of the analyzer, and an outlet 111, via which it is connected to a waste tank of the analyzer. The measuring cell 116 further comprises several radiation sources 118.1, 118.2, 118.3, 118.4 that are designed to emit measuring radiation. For example, they can each comprise a light-emitting diode. They are connected to a control and evaluation unit of the analyzer (not shown in FIG. 2) that is designed to control the radiation sources 118.1, 118.2, 118.3, 118.4 to emit measuring radiation. The radiation sources 118.1, 118.2, 118.3, and 118.4 emit measuring radiation of different wavelength ranges, i.e., each radiation source 118.1, 118.2, 118.3, 118.4 emits measuring radiation of a wavelength range that differs from the wavelength ranges of the measuring radiation emitted by the other radiation sources 118.1, 118.2, 118.3, 118.4.

The cuvette K consists of a material that is transparent to the measuring radiation of the radiation sources 118.1, 118.2, 118.3, 118.4. If the measuring radiation is within the UV/Vis range of the electromagnetic spectrum, glass or quartz glass is a suitable material.

On the other side of the cuvette K, opposite the radiation sources 118.1, 118.2, 118.3, 118.4, is arranged a detector 119, which receives measuring radiation emitted by the radiation sources 118.1, 118.2, 118.3, 118.4 after passing through the cuvette K and a liquid possibly contained in the cuvette K. The detector 119 is designed to convert the received radiation intensity of each of the radiation sources into an electrical measurement signal and to output it via the connection 120 to the control and evaluation unit of the analyzer.

An analyzer with the measuring cell 116, which is otherwise designed like the analyzer described in FIG. 1, can be used to determine a measurand correlating with a concentration of an ingredient of a measuring fluid as described above in connection with FIG. 1. In this case, in order to detect measured values, the control and evaluation unit can be designed to excite several or all radiation sources 118.1, 118.2, 118.3, 118.4 to emit measuring radiation and to thus detect several measurement signals of the detector 119 correlating with the absorption or extinction of the respectively used measuring radiation. From these measurement signals, the control and evaluation unit can determine values of the measurand.

The monitoring of the transport of the measuring fluid or other liquids into the cuvette can take place in an analyzer with the measuring cell illustrated in FIG. 2 in a manner analogous to that described above.

In the process, when the cuvette is empty, not only one (single) first measured value, but several first measured values, are detected, wherein each of the measured values is determined by exciting one of the radiation sources 118.1, 118.2, 118.3, 118.4 and by detecting by means of the detector 119 the measuring radiation intensity respectively radiated through the cuvette K. From the first measured values, a first value is determined by summation or weighted summation.

Subsequently, second measured values are detected during or after the controlling of a pump of the analyzer to transport measuring fluid from a sample receiving vessel of the analyzer into the cuvette K, wherein each of the measured values is determined by exciting one of the radiation sources 118.1, 118.2, 118.3, 118.4 and by detecting by means of the detector 119 the measuring radiation intensity respectively radiated through the cuvette K. The same radiation sources are respectively used to detect the first measured values and the second measured values. From the second measured value, a second value is determined by summation or weighted summation.

From the first and second value, a test value is determined for example, by division or by subtraction. By comparing the test value to a reference value, it can be determined, completely analogously to the method described above in which only a first and a second measured value respectively are used to monitor the liquid transport into the cuvette, whether measuring fluid was present in the cuvette K during the detection of the second measured value, or whether a sufficient volume of measuring fluid was transported into the cuvette K. If this is not the case, an error of the analyzer can be excluded.

The comparison of the test value based upon several first and second measured values to the reference value can be performed completely analogously, as before, for the test value determined from only one single first and second measured value. The reference value can, for example, in this case correspond to a value expected during the transport of a sufficient quantity of the measuring fluid into the cuvette or to the test value. The monitoring of the transport of the liquid into the cuvette K and the measures derived therefrom and performed by the control and evaluation unit, such as error messages or an interruption of the measuring operation of the analyzer, can also take place analogously.

The invention claimed is:

1. An analyzer for the determination of a measurand dependent upon the concentration of one or more ingredients of a measuring fluid, comprising:
   a measuring cell including a cuvette and a sensing element, the sensing element including a plurality of radiation sources structured to emit measuring radiation toward an at least one detector structured to generate measurement signals dependent upon an intensity of the measuring radiation impinging upon the detector, wherein the radiation sources and the detector are oriented toward each other and toward the cuvette such that the measuring radiation passes through the cuvette before impinging the detector;
   a control and evaluation unit connected to the sensing element and configured to receive the measurement signals from the sensing element and to process the received measurement signals;
   a sample receiving vessel configured to receive the measuring fluid, the sample receiving vessel connected to the cuvette via a liquid line system; and
   a delivery and metering unit in communication with the control and evaluation unit, wherein the control and evaluation unit is configured to control the delivery and metering unit to transport measuring fluid from the sample receiving vessel into the cuvette and to monitor the transport of the measuring fluid into the cuvette using the sensing element, wherein, in performing a test operation, the control and evaluation unit excites the radiation sources, detects first measurement signals of the sensing element dependent upon an intensity of the measuring radiation when the cuvette is empty, controls the delivery and metering unit to transport a specified volume of the measuring fluid from the sample receiving vessel into the cuvette, concurrently or subsequently detect second measurement signals of the sensing element dependent upon an intensity of the measuring radiation, determines a first value from the first measurement signals by summation or weighted summation, determines a second value from the second measurement signals by summation or weighted summation, determines a test value from the first value and the second value, and determines whether the test value is within a specified tolerance value range of at least one reference value stored in a memory, wherein the control and evaluation unit outputs an error or warning message if the test value is outside the specified tolerance value range.

2. The analyzer of claim 1, wherein the control and evaluation unit is configured to determine a deviation of the test value from the reference value by division or subtraction.

3. The analyzer of claim 1, wherein the control and evaluation unit is configured to compare the test value to at least one reference value stored in a memory and to monitor the transport of the measuring fluid into the cuvette based upon the comparison.

4. The analyzer of claim 1, the analyzer further comprising at least one liquid tank that contains a liquid, the at least one liquid tank connected to the cuvette via the liquid line system, wherein the control and evaluation unit is configured to detect a third measurement signal of the sensing element where the cuvette is empty, to control the delivery and metering unit to transport the liquid from the liquid tank into the cuvette, to detect a fourth measurement signal of the sensing element during or after transporting the liquid into the cuvette, and to monitor the transport of the liquid into the cuvette based upon the third and fourth measurement signals.

5. The analyzer of claim 4, wherein the liquid is a standard solution, a cleaning liquid, or a reagent to be added to the measuring fluid to determine the measurand.

6. The method of claim 1, wherein the test value is compared to at least one reference value stored in a memory, and wherein the transport of the measuring fluid is monitored based upon the comparison.

7. A method for monitoring a transport of measuring fluid into a cuvette of an automatic analyzer, comprising:
   providing an analyzer comprising:
      a measuring cell including a cuvette and a sensing element, the sensing element including plurality of radiation sources structured to emit measuring radiation toward an at least one detector structured to generate measurement signals dependent upon an intensity of the measuring radiation impinging upon the detector, wherein the radiation sources and the detector are oriented toward each other and toward the cuvette such that the measuring radiation passes through the cuvette before impinging the detector;
      a control and evaluation unit connected to the sensing element and configured to receive the measurement signals from the sensing element and to process the received measurement signals;
      a sample receiving vessel configured to receive the measuring fluid, the sample receiving vessel connected to the cuvette via a liquid line system; and
      a delivery and metering unit in communication with the control and evaluation unit;
   using the control and evaluation unit, controlling the delivery and metering unit to transport measuring fluid from the sample receiving vessel via the liquid line system into the cuvette;
   using the control and evaluation unit, monitoring the transport of the measuring fluid into the cuvette with the sensing element; and performing a test operation by:
   exciting the radiation sources to radiate measuring radiation into the cuvette and detecting first measurement signals dependent upon an intensity of the measuring radiation after passing through the cuvette where the cuvette is empty;
during or after controlling the delivery and metering unit to transport a specified volume of measuring fluid into the cuvette, exciting the radiation sources to radiate
   measuring radiation into the cuvette and detecting second measurement signals dependent upon the intensity of the measuring radiation after passing through the cuvette;
   determining a first value from the first measurement signals by summation or weighted summation;
   determining a second value from the second measurement signals by summation or weighted summation;
   determining a test value from the first value and the second value by subtraction or division;
   determining whether the test value is within a specified tolerance range of at least one reference value stored in memory, and
   outputting an error or warning message if the test value is outside the specified tolerance value range.

8. The method of claim 7, the method further comprising, using the second measurement signals, detecting when a liquid-air boundary traversing the cuvette during the transporting of the measuring fluid into the cuvette passes a beam path extending between the at least one radiation source and the detector, the beam path extending substantially orthogonal to a direction of movement of the liquid-air boundary.

* * * * *